United States Patent [19]

Nambu et al.

[11] Patent Number: 5,012,503

[45] Date of Patent: Apr. 30, 1991

[54] METHOD FOR STERILIZATION OF POLYVINYL ALCOHOL GEL BY GAMMA-RAY

[75] Inventors: Masao Nambu; Tadayuki Onishi, both of Yokohama; Masayuki Onohara, Ibaraki, all of Japan

[73] Assignees: Sumitomo Bakelite Company, Ltd.; Nippon Oil Company, Ltd., both of Minato, Japan

[21] Appl. No.: 233,660

[22] PCT Filed: Nov. 4, 1987

[86] PCT No.: PCT/JP87/00847

§ 371 Date: Jul. 1, 1988

§ 102(e) Date: Jul. 1, 1988

[87] PCT Pub. No.: WO88/03414

PCT Pub. Date: May 19, 1988

[30] Foreign Application Priority Data

Nov. 5, 1986 [JP] Japan .................. 61-261794

[51] Int. Cl.$^5$ .............................................. G21K 5/00
[52] U.S. Cl. ...................................................... 378/64
[58] Field of Search ........... 378/64; 250/432 R, 455.1, 250/433, 434; 528/481; 526/936; 523/105, 136–137; 521/141; 525/56, 62

[56] References Cited

U.S. PATENT DOCUMENTS

| | | | |
|---|---|---|---|
| 2,855,517 | 10/1958 | Rainer et al. ................ | 378/64 |
| 3,758,273 | 9/1973 | Johnston et al. ............. | 378/64 |
| 3,852,032 | 12/1974 | Urbach ....................... | 250/455.1 |
| 4,110,185 | 8/1978 | Williams et al. ............. | 378/64 |
| 4,472,542 | 9/1984 | Nambu ........................ | 528/481 |
| 4,664,857 | 5/1987 | Nambu ........................ | 264/28 |
| 4,734,097 | 3/1988 | Tanabe et al. . | |
| 4,808,353 | 2/1989 | Nambu et al. ................ | 264/28 |

FOREIGN PATENT DOCUMENTS

| | | |
|---|---|---|
| 0107055 | 5/1984 | European Pat. Off. . |
| 47-12854 | 4/1972 | Japan . |
| 36630 | 3/1983 | Japan . |
| 177066 | 9/1985 | Japan . |

OTHER PUBLICATIONS

"NMR Igaku", NMR Medical Science, vol. 5, No. 2, 1985, pp. 85–90, English summary included.

"A New Polyvinyl Alcohol Hydrogel . . ." by Klim et al., American Journal of Opthalmology, vol. 100, No. 2, (8/1985), pp. 328–330.

"New Disposable Electroretinographic . . . Polyvinyl Alcohol Gel" by Honda et al., Amer. Jour. of Opthalmol., vol. 99, No. 4 (4/1985), pp. 492–493.

"Mol", vol. 86, No. 6, 1986, pp. 86–91, English summary included.

"Kobynshi", (Polymer), vol. 35, p. 87, (1986), English summary included.

"Jeti", vol. 33, No. 9, 1985, pp. 45–49, English summary included.

*Primary Examiner*—Craig E. Church
*Attorney, Agent, or Firm*—Browdy and Neimark

[57] ABSTRACT

This invention relates to a method for sterilization, by irradiation with γ-ray, of a hydrogel obtained by freezing an aqueous polyvinyl alcohol solution and then thawing it or by partially dehydrating (3% or more in weight reduction rate of the frozen body) the aqueous polyvinyl alcohol solution as it is frozen under vacuum and by selecting dosage of the γ-ray of 3–10 Mrad, stable sterilization effect can be obtained with less soluble decomposition products. Especially, this method is effective and most suitable as a method for sterilization of polyvinyl alcohol hydrogel molded article for medical use.

3 Claims, No Drawings

METHOD FOR STERILIZATION OF POLYVINYL ALCOHOL GEL BY GAMMA-RAY

TECHNICAL FIELD

This invention relates to a method for sterilization of polyvinyl alcohol gel and more particularly it relates to a method for γ-ray sterilization of hydrogel obtained by freezing and thawing of aqueous polyvinyl alcohol solution or by partial dehydration under vacuum of aqueous polyvinyl alcohol solution in frozen state wherein sterility harmless for living tissues can be obtained by avoiding by-production of soluble γ-ray decomposition products.

BACKGROUND ART

Sterilization, pasteurization and disinfection are essential for medical materials which contact directly or indirectly with living tissues. Various methods of sterilization, pasteurization and disinfection have been proposed and it is well known that either one of them is employed depending on properties of medical materials and purposes of use thereof and efforts have been made to ensure and accomplish safety and innocuousness of materials.

Among these methods, advantages of γ-ray sterilization method are noticed in that the method can sterilize the materials through container in which the materials are completely enclosed and besides the method is effective for bacterial spores high in heat resistance and further Pseudomonas aeruginosa, spores of tubercle bacillus and Gram-negative bacteria which often show resistance against medicines (disinfectants) and the γ-ray sterilization method is considered to have high reliability in sterilization of rubber articles and plastic articles (general polymer materials poor in heat resistance) to which is difficult to apply high pressure steam sterilization method and dry sterilization method.

As the method which comprises enclosing a non-heat resistant material in a container made of plastic film and then sterilizing the material through the container, gas sterilization method with ethylene oxide is famous and is widely used in hospitals and medical device makers. In this case, it is necessary to perform desorption of residual gas adsorbed to materials carefully and over a long period of time and further to keep watch to ensure that amount of still remaining ethylene oxide (and ethylene glycol, ethylene chlorohydrin, etc. as modification components thereof) is less than permissible limits. Especially, when this gas sterilization method is applied to sterilization of hydrogels (water-containing gels) represented by polyacrylamide, much care must be taken for discharge of a large amount of gas dissolved in water as well as adsorbed gas. Although it can be said that regulation value can be met (degassing to 2000 ppm), there is some fear of remaining toxicity which may cause hemolysis and thrombus.

γ-ray sterilization method does not require operation for removal of residual toxin as required in the above gas sterilization method and disinfection with chemicals (ethyl alcohol, formalin, glutaraldehyde, chlorohexidine, benzalkonium chloride, etc.) and hence, merits as sterilization method for non-heat resistant medical materials have been widely recognized. However, it has been warned that irradiation of a large quantity of γ-ray results in denaturation (radical decomposition and oxidation decomposition of materials) of most of rubbers and plastics to produce soluble (water-soluble) low molecular weight deterioration products and furthermore, mechanical strength of the materials per se often decreases. (Takuma Ohba; "Kobunshi", 22, 607 (1973)).

The phenomena of formation of radicals due to irradiation with γ-ray, which cause deterioration by oxidation in which coexisting oxygen participates have been confirmed in natural polymers (protein) and synthetic polymers and aqueous solutions of these polymers. [See, P. S. Elias et al (translators, Rikimaru Hayashi et al); "Shokuhin Shosya no Kagaku" ("Chemistry of Irradiation of Food", p. 11 (1981) published from Gakkai Shuppan Center; Mineo Sado, "Ikishi" (J. Medical Instruments) 55, 480 (1985); and Kenji Sato, "Rinshoishi" (J. Clinics), 11, 422 (1985)]. Further, it was attempted to conduct irradiation without oxygen (air) (in nitrogen atmosphere) in order to avoid deterioration due to oxidation, but this also results in considerable deterioration and denaturation (due to radical decomposition) of both protein and synthetic polymer and besides there is a tendency of increase in γ-ray resistance of microorganisms in nitrogen atmosphere and irradiation of larger quantity of γ-ray for complete sterilization promotes radical decomposition of materials.

Considering these problems, irradiation dosage necessary and sufficient and minimum for accomplishing the purpose of sterilization and confining decomposition of materials to the minimum (permissible limit) has been searched and sterilization effect with dosage of 0.6–2.5 Mrad has been investigated, for example, on pad (0.76–1.1 Mrad) and catheter, injection cylinder, surgical suture, dialyser for kidney dialysis, infusion set and glove (2–2.5 Mrad). Thus, since generally deterioration (decomposition) of materials is accelerated with increase of irradiation dosage, it has been guided to decrease initial number of living bacteria (before sterilization) as small as possible and to keep γ-ray dosage at less than 2.5 Mrad. [See, Takuma Ohba, "Kogyo Zairyo" (Industrial Materials), 25 (2), 65 (1977); "Kobunshi" (Polymer), 22, 607 (1973); Kenji Sato, "Rinshoishi" (J. Clinics), 11, 422 (1985); Mineo Sado, "Gosei Jushi" ("Synthetic Resin" 31, (5), 12 (1985); Fumio Yoshii et al, "Ikishi" (J. Medical Instruments), 55, 251 (1985); and Yoshio Iwasaki et al, "Ikishi" (J. Medical Instruments), 55, 244 (1985)].

On the other hand, as hydrogel innocuous for living organisms, there have been proposed a gel obtained by freezing and thawing aqueous polyvinyl alcohol solution and a gel obtained by partial dehydration in vacuo of aqueous polyvinyl alcohol solution as it is in frozen state. These gels are expected to be useful as supplement (for prevention of adhesion) for defects in lung thymus, pericardium, duramater and artificial trachea, artificial gullet, artificial cartilage, electrodes for embedding ocular conjunctiva and cornea, membranes for preventing adhesion of tendon, materials for suture of sclera, electrodes for artificial internal ear, denture-base, supplement for upper and lower jaws, membranes for preventing adhesion of joints, catheters for gullet, rectum and vagina. [See "NMR Igaku" (NMR Medical Science) 5 (2), 85 (1985); "Am. J. Ophthalmology", 100, 328 (1985) and 99, 492 (1985)].

As process for producing such polyvinyl alcohol hydrogels, for example, Japanese Patent Kokoku No. 47-12,854 and Japanese Patent Kokai Nos. 59-56,446 and 60-177,066 disclose frozen and thawed gels and Japanese Patent Kokai Nos. 57-130,543 and 58-36,630 disclose gels obtained by partial dehydration in vacuo in the frozen state. These hydrogels are obtained as insoluble rubbery materials with mechanical strength and flexibility similar to flexible tissues of living organisms by subjecting aqueous polyvinyl alcohol solution to merely freezing and thawing or freezing, keeping in vacuo and thawing without any chemical treatments. These are specific hydrogels which are highly inert to living tissues and do not cause reaction with foreign materials, infiltration into cells, inflammation and stimulus and which can function as a substitute for gullet when implanted in the gullet which is considered to be strongest in elimination action among various organs. However, since these hydrogels do not undergo chemical crosslinking and have rubbery state merely by crystallites supposed to be produced at interlocking points of polymer in the production step ["Kobunshi Kako" (Polymer processing), 32, 523 (1983)], heat resistance cannot be expected and both the high pressure steam sterilization and the dry sterilization cannot be applied thereto. Further, they contain a large amount of water and so it is difficult to release the remaining dissolved gas after gas sterilization.

Thus, γ-ray sterilization method is naturally expected. However, it has been found that when this hydrogel is irradiated with γ-ray of the aforesaid target value (2.5 Mrad or less), considerable amount of water-soluble deterioration products are by-produced. That is, there have been experienced many cases where content of soluble matters (decomposition products) in the gel is as high as 0.02–0.03 wt % according to analysis (KMnO$_4$ titration) of warm water extracts based on standard for medical artificial vessel (Notification No. 298 of the Welfare Ministry). The amount of soluble matters reduces to $\frac{1}{3}$–1/100 with decrease in irradiation dosage of γ-ray to 0.1–0.2 Mrad, but it is impossible to surely accomplish the sterilization by the irradiation dosage of less than 0.3 Mrad.

DISCLOSURE OF INVENTION

This invention provides a safe and sure method or γ-ray sterilization according to which by-production of decomposition (deterioration) products is prevented for said polyvinyl alcohol gel excellent in adaptability to living organisms and the desired purpose of sterilization can be accomplished.

According to this invention there is provided a method for sterilization with a little by-production of decomposition (deterioration) products which comprises irradiating with γ-ray a hydrogel obtained by subjecting an aqueous polyvinyl alcohol solution to freezing, thawing or by subjecting an aqueous polyvinyl alcohol solution as it is frozen to partial dehydration in vacuo of at least 3% in dehydration rate (weight reduction rate of frozen body) wherein γ-ray irradiation dosage is 3–10 Mrad, preferably 3.5–7 Mrad.

This invention will be explained in more detail below.

As a result of detailed examination of the above method of γ-ray sterilization of hydrogel, it was found that with gradual increase in dosage from 0.1 Mrad to 2.5 Mrad the by-production of deterioration products (soluble decomposition products, deterioration products with oxidation) often extremely increased, for example, 0.008%, 0.016%, 0.02% and 0.028% of deterioration products were produced in the gel with 0.1 Mrad, 1 Mrad, 1.5 Mrad and 2.5 Mrad, respectively. In this case, it was infrequently experienced that only 0.0003%, 0.0015%, 0.0015% and 0.0015% were produced with 0.1 Mrad, 1 Mrad, 1.5 Mrad and 2.5 Mrad, respectively and reproduction thereof was tried. However, the reproduction probability was low irrespective of the dosage rate (0.1–1 Mrad/hour) and irradiation atmosphere (air or nitrogen, oxygen, helium) and even if the dosage was severely fixed, the amount of by-produced deterioration products greatly varied between the values of above examples as the maximum and minimum values. Investigation of causes for this variation is very difficult because deterioration products are in a slight amount, namely, only less than 2.8 ppm in extract water and further, they are not single component and no clue has yet been found. However, it can be supposed that in the present case where a slight amount of product at very early stage of radical reaction is dealt with, the reaction is, of course, in non-steady state and besides, the transient passage per as cannot be expected to have reproduction accuracy.

In any way, as far as medical materials are handled, sterilization requires support by secure technique which can ensure formation of sterility and can keep amount of deterioration products as small as possible. In order to meet the regulation for dissolving-out substances of artificial vessels (2 ml in amount of 0.01 N-KMnO$_4$ consumed for extract solution), it is concluded that amount of deterioration products in gel must be 0.038% or less and γ-ray sterilization method which produces 0.02–0.028% of deterioration products which may approach the target value of said 0.038% or less cannot be simply employed without sufficient investigation.

There are known a number of basic studies on reaction theory for irradiation of γ-ray on aqueous polyvinyl alcohol solution and all of them reported scission of polymer chain and deterioration by oxidation and decomposition phenomena. It is well known that crosslinking phenomenon occurs at this time and an attempt was made to experimentally pour the thus produced fluid soft gel into an eyeball of rabbit as a filling liquid in eyeball (vitreous body fluid). [See "Nippon Ganka Gakkaishi" (J. Japan Ophthalmology Society), 83, 1478 (1979), "Nippon Ganka Kiyo" (Japan Ophthalmology Bulletin), 29, 1922 (1978); 35, 1340 (1984)]. In all of other studies, such fluid soft gels are obtained and they repeatedly disclosed methods of increasing chances for interaction (leading to crosslinking) between polyvinyl alcohol molecules by increasing polyvinyl alcohol) concentration in water up to 0.3~2.0% in an attempt to avoid conditions at which decomposition and deterioration of polyvinyl alcohol dissolved in water proceed. However, none of them deal with a slight amount (0.028% or less) of deterioration products (water-soluble decomposition products) produced in water-insoluble hydrogel as in this case. Besides, they made no research on mechanism of side-reaction and countermeasure for suppressing it.

This invention is characterized by ensuring a dosage more than 2.5 Mrad with ignoring the common sense in techniques for γ-ray sterilization of natural polymers and synthetic polymers. In irradiation of γ-ray according to this invention, dosage rate may be the ordinary 0.1–1 Mrad/hour and can be, for example, 0.3–0.8 Mrad/hour, preferably 0.5–0.7 Mrad/hour. Moreover, γ-ray irradiation temperature in this invention can be from normal temperature (room temperature) to 40° C. as in the usual sterilization operation and it is not needed to keep especially low temperature as needed in crosslinking (gelation) of aqueous polyvinyl alcohol solution by irradiation with γ-ray.

Materials to which this invention can be applied include frozen thawed gel of said aqueous polyvinyl alcohol solution and hydrogel obtained by subjecting aqueous polyvinyl alcohol solution as it is frozen to partial dehydration in vacuo. As the polyvinyl alcohol, there may be used ordinarily commercially available products having a saponification degree of 95 mol % or more and an average polymerization degree of 1,000 or more (maximum average polymerization degree: 2500–3000). The saponification degree is preferably as close to 100 mol % as possible because hydrogels superior in characteristics such as strength can be obtained, but 95 mol % or more is sufficient. With reference to the average polymerization degree, commercially available products can be used without any difficulty even of the classes of maximum polymerization degree, but when it is less than 1000, the resulting hydrogel is inferior in characteristics. Concentration of polyvinyl alcohol in the aqueous solution which is to be subjected to freezing can be more than 8 wt % and not more than 50 wt %.

Freezing temperature can be optional temperatures lower than 0° C., preferably −10° C. or lower. The aqueous polyvinyl alcohol solution is poured into a shaping mold of optional shapes and then is cooled to −10° C. or lower to solidify and mold it and then is thawed to obtain a frozen and thawed gel. The gel obtained at this stage is often insufficient in mechanical strength depending on use, especially in tear strength enough to use for suturing. The strength can be greatly increased by repeating the freezing and thawing to reach a cumulative freezing number of 2–8. [See "MOL" 86, (6), 86 (1986); "Kobunshi" (Polymer), 35, 87 (1986)]. The strength approaches to a certain value by repetition of freezing and thawing and shows nearly a constant value by repetitions of 9 or more times.

The frozen and partially dehydrated gel as hydrogel to which this invention can be applied is obtained by subjecting said frozen and solidified body of aqueous polyvinyl alcohol solution to partial dehydration in vacuo of 3 wt % or more in dehydration rate (weight reduction rate of solidified and molded body) without melting the frozen and solidified body. [See "JETI", 33 (9), 45 (1985)]. In this case, mechanical strength of the resulting gel markedly enhances with increase in dehydration rate, but considering that the gel is used in contact with living soft tissue, too much hardening is not preferred and high water content gel useful as medical materials such as, for prosthesis of living tissues is obtained by dehydration of, normally, 3–30%, preferably 5–20%.

The hydrogel in this invention is previously molded into shapes adapted to uses by pouring aqueous polyvinyl alcohol solution in a mold, but it may be molded into general shapes such as sheet, tube and the like and cut to desired shapes on use or may be coated on a molded article of plastics and the like. In the case of membrane for prosthesis of living tissue or for prevention of adhesion, the gel is molded to a thickness of about 0.3–2.0 mm. However, for some uses, it may be molded product of greater thickness and having specific shapes.

As explained above, in the hydrogel dealt with by this invention, the polyvinyl alcohol single component is used as gel material (gelling component). However, if necessary, a component which does not prevent gelation of polyvinyl alcohol may coexist and amount thereof can be, for example, ½ or less of polyvinyl alcohol. As the component which does not prevent gelation of polyvinyl alcohol, mention may be made of, for example, antibiotics such as penicillin and fradiomycin and medicines such as polymyxin B, and chondroitin sulfate, and potassium hyaluronate. For embedding them in hydrogel, these components as they are or as aqueous solution or suspension ca be previously added to aqueous polyvinyl alcohol solution, then stirred and homogeneously dispersed and thereafter, subjected to the aforesaid freezing and subsequent treatments.

It can be said to be a preferred embodiment to carefully and repeatedly wash the thus obtained hydrogel with a sterilized water or a physiological saline for injection at room temperature to 50° C. prior to subjecting the hydrogel to the sterilization of this invention for reduction of living bacteria (and dead bacteria) adhering to the gel. Furthermore, for prevention of hemolysis, it is also a preferred embodiment to dip the gel before sterilization in physiological saline of room temperature to 50° C. for 10 minutes or more to replace most of water contained in the gel.

It is desired that the thus carefully produced polyvinyl alcohol hydrogel product is enclosed in a bag made of a material superior in oxygen barrier properties such as an aluminum-polyethylene laminate film, then the bag is deaerated to produce vacuum state or air is replaced with an inert gas such as nitrogen and the bag is sealed and thereafter, this is irradiated with γ-ray.

EFFECT OF THE INVENTION

When the polyvinyl alcohol gel is sterilized with γ-ray according to this invention, all microorganisms such as bacteria, yeasts and fungi can be killed and besides, decomposition of materials which ordinarily inevitably occur when sterility is accomplished is most completely prevented and total amount of deterioration products extracted with warm water can be always and securely kept at less than 0.0095% of the gel (material to be sterilized). According to this invention, irrespective of dosage rate, thus, under normal γ-ray irradiation dosage rate (0.1–1 Mrad/hour, preferably 0.5–0.7 Mrad/ hour), by-production of deterioration products can be effectively inhibited and no special auxiliary means are needed such as temperature control at irradiation. These are merits of this invention.

The method which can surely sterilize hydrogel and can always control the by-production rate of deterioration products at 0.0095% or less has been firstly provided by the present inventors.

BEST MODE FOR CARRYING OUT THE INVENTION

Examples of this invention will be explained below. The % is by weight.

EXAMPLE 1

A 29% aqueous solution (NaCl 0.9%) of polyvinyl alcohol of 2,000 in average polymerization degree and 99 mol % in saponification degree was poured into a film-forming mold, frozen by cooling to −30° C. and then thawed. This series of freezing and thawing was repeated until cumulative freezing number reached 7 times. In this way, ten supplement films for defect portion of pericardium which were 0.5 mm thick and 10 cm square were prepared.

In a 500 ml conical flask which had been sterilized was charged 500 ml of a sterilized physiological saline for injection, in which the ten gel films obtained above were dipped and allowed to stand for 24 hours at 40° C.

The physiological saline in the conical flask was replaced by a fresh one and the content was left to stand for further 24 hours and washing was carried out twice. Then, each of the gel films was put in a bag made of a polyethylene-aluminum foil laminate film and this bag was sealed up. Then, this was subjected to γ-ray sterilization at a dosage rate of 0.6 Mrad/hour and an irradiation dosage of 3.5 Mrad.

One gram was cut out from each of the thus obtained ten sterilized gel films and dipped in 100 g of deionized water and left to stand at 37° C. for 24 hours. Then, consumption amount of $0.01N$-$KMnO_4$ was obtained for aqueous phase in accordance with standard for medical artificial vessel (Notification No. 298 of the Welfare Ministry) to find that the amount was only 0.20–0.40 ml for all samples which completely meet the regulation value of 2.0 ml. Presuming that polyvinyl alcohol (fragment) extracted from the gel film is converted to oxalic acid by $KMnO_4$ [See H. Staudinger et al; "Chem. Ber.", 60, 1282 (1927)]. It has been found that the above $KMnO_4$ consumption amount (0.20–0.40 ml) is merely 0.11–0.22 ppm as polyvinyl alcohol (fragment) in the extract solution and is a slight amount of 0.0011–0.0022% in terms of concentration of water-soluble matter in the gel. Furthermore, it has been found that even if it is supposed that the extracted polyvinyl alcohol (fragment) undergoes breakage of main chain by $KMnO_4$ and carbonylation of hydroxyl group [See seiichi Okamura et al. "Koka" (Industrial Chemistry), 45, 1107 (1942); Sakurada and Matsuzawa, "Kobunshi Kagaku" (Polymer Chemistry), 16, 633 (1959)], the $KMnO_4$ consumption amount above mentioned is merely 0.37–0.74 ppm as polyvinyl alcohol in the extract solution and 0.0037–0.0074% in terms of concentration in the gel.

No changes were seen in dynamic elastic moduls ($3 \times 10^5$ N/M$^2$), tensile break strength (28–30 kg/cm$^2$) and break extension (210–260% by length) of the film before and after the sterilization and these properties did not deteriorate even after lapse of 1 year from the sterilization, but rather were somewhat improved (20–30%). Even if this is due to hardening phenomenon caused by radical reaction by irradiation with γ-ray, it has been concluded changes in properties of such degree give no problems for use of this film.

For all of the samples just after sterilization, no microorganisms were detected in both of sterility test media of thioglycollic acid medium I and glucose peptide medium according to Japanese pharmacopeia.

COMPARATIVE EXAMPLE 1

In accordance with Example 1, ten hydrogel films were prepared and subjected to γ-ray sterilization with an irradiation dosage of 2.5 Mrad and $KMnO_4$ consumption amount was measured in similar manner to obtain 1.6 ml maximum, 0.3 ml minimum and 0.83 ml average. There were three examples in which the amount exceeded 1.5 ml. These were considered to cause problems because the amount was close to 2.0 ml of the standard for medical artificial vessel.

COMPARATIVE EXAMPLE 2

In accordance with Comparative Example 1, ten gel films were prepared and were subjected to the γ-ray sterilization with a dosage of 1.5 Mrad and $KMnO_4$ consumption amount was obtained to find that maximum was 1.1 ml, minimum was 0.1 ml and average was 0.7 ml and there were four examples where the amount exceeded 1 ml. Exceeding 1.5 ml was avoided by reducing the dosage, but it was judged that considering the four examples where the amount exceeded 1 ml and was close to 2.0 ml of the standard for medical artificial vessel, there were problems even if sterility could be attained by such an irradiation dosage.

COMPARATIVE EXAMPLE 3

In accordance with Comparative Example 1, ten gel films were irradiated with 0.5 Mrad of γ-ray and $KMnO_4$ consumption amount was obtained to find that maximum amount was 0.5 ml, minimum amount was 0.1 ml and average amount was 0.3 ml and the amount was 0.5 ml or less in all examples. It was concluded in combination with Comparative Examples 1 and 2 that with decrease in irradiation dosage the $KMnO_4$ consumption amount also decreases and amount of water-soluble decomposition products sharply decreases, but there was difficulty in ensuring always sterilization (sterility) by such low dosage. In fact, microorganisms were detected from three gel films just after irradiation.

EXAMPLE 2

314 Grams of 18.6% aqueous solution of polyvinyl alcohol having an average polymerization degree of 1,000 and a saponification degree of 98 mol % was poured into a mold for molding a disc of 0.5 mm thick and 20 cm in diameter and cooled to $-30°$ C. to obtain a frozen body. Under a reduced pressure of 0.1 mmHg, 2 g of water was removed from respective molds (15 molds in total) and temperature was returned to room temperature to obtain a disc-like gel of 79% in water content, which was put in a closed container. This water content nearly the same as that (78–81%) of skeletal muscle, small intestine, stomach, uterine, kidney, etc. of human beings.

Then, this disc was put in a bag of polyethylene film and the bag was sealed and this was subjected to γ-ray sterilization with 3 Mrad. Then, the bag was opened and partially cut place (10 g) of the disc was transferred to a broth medium and cultured at 37° C. for 7 days, but no microorganisms were detected. Another portion (1 g) of the disc was extracted with warm water and $KMnO_4$ consumption amount was obtained in accordance with Example 1. For 15 samples, maximum amount was 0.4 ml, minimum amount was 0.2 ml and average amount was 0.3 ml. As in Example 1, difference between the maximum amount and minimum amount was small and the amount was much lower than the standard value (2.0 ml). Thus, it was concluded that the products were surely reliable.

EXAMPLE 3

Ten gel films prepared in accordance with Example 1 were irradiated with γ-ray of 10 Mrad in similar manner. No conspicuous changes in properties (dynamic elastic modulus, stress relaxation, tensile break strength and extension (%) were recognized before and after the sterilization. $KMnO_4$ consumption amount for warm water extract was as follows: maximum 0.3 ml, minimum 0.1 and average 0.2 ml.

That is, although dosage was increased to more than 3 times those in Examples 1 and 2, $KMnO_4$ consumption amount did not increase and rather, as a result of separate experiments of irradiation with 4, 5, 7 and 8 Mrad, there was recognized the tendency of reduction, though slight, of $KMnO_4$ consumption amount with increase in irradiation dosage within the range of 3–10 Mrad.

Industrial Applicability

As explained above, this invention has succeeded in complete sterilization with γ-ray of medical molded articles of polyvinyl alcohol hydrogel used as non-heat resistant medical materials by selecting a irradiation dosage of γ-ray within the range of 3-10 Mrad.

We claim:

1. A method for sterilization of polyvinyl alcohol gel while decreasing by-product deterioration rates to about 0.0095% or less comprising: irradiating with γ-ray,
   (A) a hydrogel obtained by freezing thawing an aqueous polyvinyl alcohol solution so that the number of times of accumulative freezing amounts to 2-8 times, or
   (B) a hydrogel in a range of dehydration rate of 3-30% obtained by subjecting an aqueous polyvinyl alcohol solution in the frozen state to vacuum partial dehydration; wherein the irradiation dosage of γ-ray is from about 3.5 to about 7 Mrad.

2. A method for sterilization of polyvinyl alcohol while decreasing by-product deterioration rates to about 0.0095% or less comprising taking a medical hydrogel molded product of polyvinyl alcohol in a range of dehydration rate of 3-30% obtained by pouring an aqueous polyvinyl alcohol solution having a saponification degree of 95 mol % or more and an average polymerization degree of 1000 or more in a mold and repeatedly freezing thawing it so that the number of times of accumulative freezing amounts to 2-8 times or subjecting the aqueous polyvinyl alcohol solution in the frozen state to vacuum partial dehydration, putting frozen state material in a bag or container having oxygen barrier properties, deaerating the bag or container to produce a vacuum or place inert gas therein, sealing the bag or container and irradiating with γ-rays of from about 3.5 to about 7 Mrad.

3. A method for sterilization of polyvinyl alcohol gel according to claim 2 wherein the hydrogel molded product contains a medicine embedded therein.

* * * * *